United States Patent
Wolfe

[11] Patent Number: 5,879,693
[45] Date of Patent: Mar. 9, 1999

[54] INDIVIDUALLY PACKAGED DISPOSABLE SINGLE ACNE PAD

[75] Inventor: David M. Wolfe, Hollywood, Fla.

[73] Assignee: Circle Laboratories, Inc., Hollywood, Fla.

[21] Appl. No.: 791,827

[22] Filed: Jan. 30, 1997

[51] Int. Cl.[6] ............................. A01N 25/34; A61L 15/16
[52] U.S. Cl. .......................... 424/402; 424/443; 424/446
[58] Field of Search .................................. 424/402, 443, 424/446

[56] References Cited

U.S. PATENT DOCUMENTS

| | | | |
|---|---|---|---|
| 4,749,080 | 6/1988 | Toohey | 206/210 |
| 4,891,227 | 1/1990 | Thaman et al. | 424/443 |

Primary Examiner—Thurman K. Page
Assistant Examiner—Kathryne E. Shelborne
Attorney, Agent, or Firm—Jack E. Dominik

[57] ABSTRACT

Packaging an acne packet, which packet will hold just one three inch by three inch square acne pad is disclosed. The three inch square acne pad is folded in half twice to render the size of the acne pad one and one-half inches by one and one-half inches. The, folded pad is thereafter inserted by a packet forming machine utilizing MP3850 paper, foil, and poly carbonate to render the packaged pad ultimately three inches by two and three-quarters by one-eighth to one-quarter inch thick with twenty-two individual packets separated at their lateral edges and then placed in a box. The acne pad itself is 75 gram 149–189 tight waffle Novonette. Each pad is impregnated with 1.56 grams of the treatment solution. The method of forming the pads is to run the three inch ribbon of waffle Novonette through a feeding machine and thereafter dip the same in a solution having as its most active ingredient 0.5% salicylic acid. De-ionized water (75%) and SD Alcohol 40 (24%) make up the major portion of the inactive ingredient.

2 Claims, 2 Drawing Sheets

INDIVIDUALLY PACKAGED DISPOSABLE SINGLE ACNE PAD

FIELD OF THE INVENTION

The present invention relates to acne pads used primarily for facial cleansing with the intent of removing or reducing dirt or oil and improving the cleanliness of acne blemished skin. The invention further relates to the formation of the pad, the packaging of the pad, the selection of the pad material as well as the cleansing contents, and the proportioning of the same.

SUMMARY OF THE PRIOR ART

Acne pads have been known and marketed for several years. The common form is a plurality of the circular pads soaked in a cleansing solution. The circular pads are stacked on top of each other. Normally the number of pads is fifty to seventy-five. Thereafter, they are packaged in a plastic cylindrical-type jar with a screw top.

Exemplary of the prior art is the "Stridex" (registered trademark of Bayer Corp., Consumer Care Division, Myerstown, Pa.) circular acne pad which are packaged in a stack of fifty-five with a diameter of two and seven-sixteenths inches and held in a re-closable screw top plastic jar.

The principal problem of the prior-art acne pads has been their lack of portability. When a jar is three inches in diameter and over three inches high it is bulky, difficult to hold in the pocket or in the purse of a female user. Moreover, where there is a stack of pads employed, leakage invariably occurs with a resulting diminution of the potency of the pad. Indeed, contact with the hand can also result in partial contamination. In addition the jar-type configuration cannot be broken up for carrying, such as two to six pads being stored in a sandwich bag or otherwise wrapped for storage in the wallet, or pocket. In addition, if the screw top cover is left off for any particular period of time, evaporation occurs and significantly reduce the potency of the remaining fluid contents of the jar. Finally, the circular acne pads waste that portion of the substrate that must be cut to render the pad circular. Because the prior art circular pads have no corners to penetrate remote areas such as behind the ear, the crease at the nose, and elsewhere. Moreover, a three inch square utilizes nine square inches, whereas a three inch circle utilizes slightly over seven square inches. The saving in material is approximately 28%.

SUMMARY OF THE INVENTION

The present invention relates to packaging an acne packet, which packet will hold just one three inch by three inch square acne pad. The three inch square acne pad is folded in half twice to render the size of the acne pad one and one-half inches by one and one-half inches. The folded pad is thereafter inserted by a packet forming machine utilizing MP3850 paper, foil, and poly carbonate to render the packaged pad ultimately three inches by two and three-quarters by one-eighth to one-quarter inch thick with twenty-two individual packets separated at their lateral edges and then placed in a box. The acne pad itself is 75 gram 149–189 tight waffle Novonette. Each pad is impregnated with 1.56 grams of the treatment solution. The method of forming the pads is to run the three inch ribbon of waffle Novonette through a feeding machine and thereafter dip the same in a solution having as its most active ingredient 0.5% salicylic acid. De-ionized water (75%) and SD Alcohol 40 (24%) make up the major portion of the inactive ingredient.

In view of the foregoing it is a principal object of the present invention to provide for portable individually packaged acne pads which permit more flexibility in carrying, using, and storing.

Yet another object of the present invention relates to providing packets of acne pads which are effective in usage, and can be used one at a time without cross-contamination or otherwise effecting the totally sealed configuration of the remaining acne pads.

BRIEF DESCRIPTION OF THE ILLUSTRATIVE DRAWINGS

The present invention will be more fully understood taken in conjunction with the accompanying illustrative drawings, in which.

DESCRIPTION OF A PREFERRED EMBODIMENT

Figure 1:
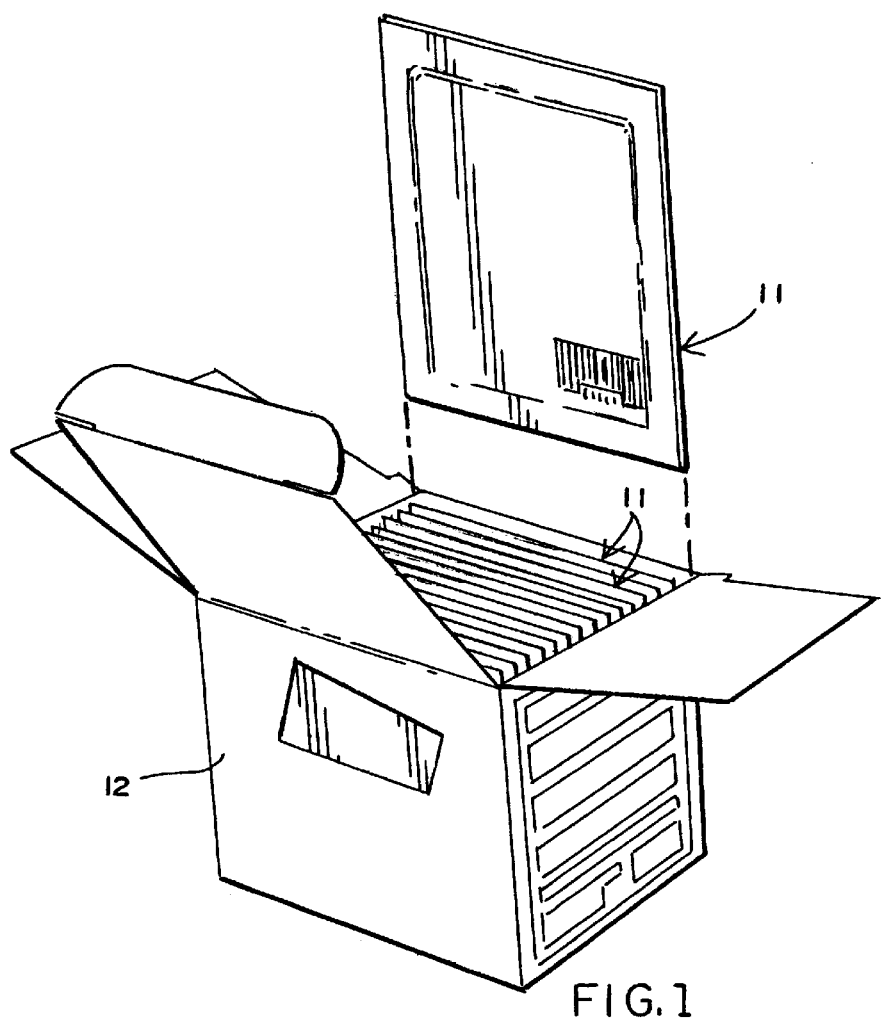
FIG. 1 is a perspective view showing the acne packets immediately above the ultimate packaging for twenty-two packets.
Figure 2:
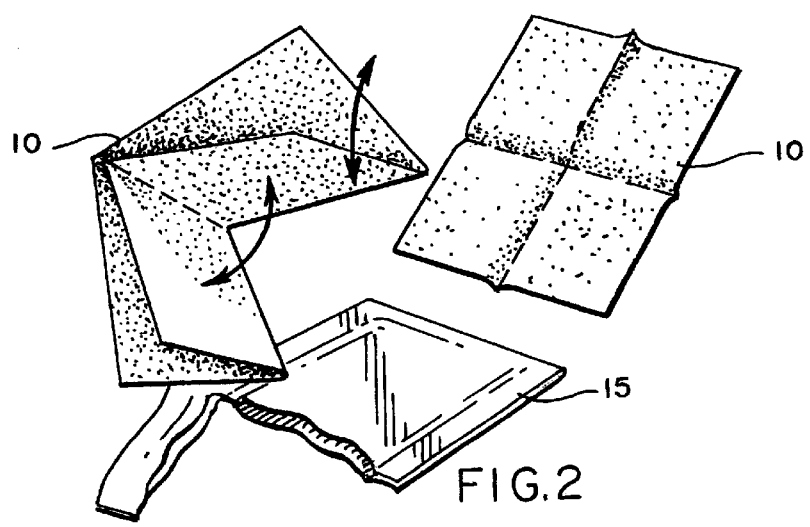
FIG. 2 is an exploded perspective view showing an individual packet after having been opened and illustrating how the three inch square has been folded twice to render the packaged portion one and one-half inches by one and one-half inches.
Figure 3:
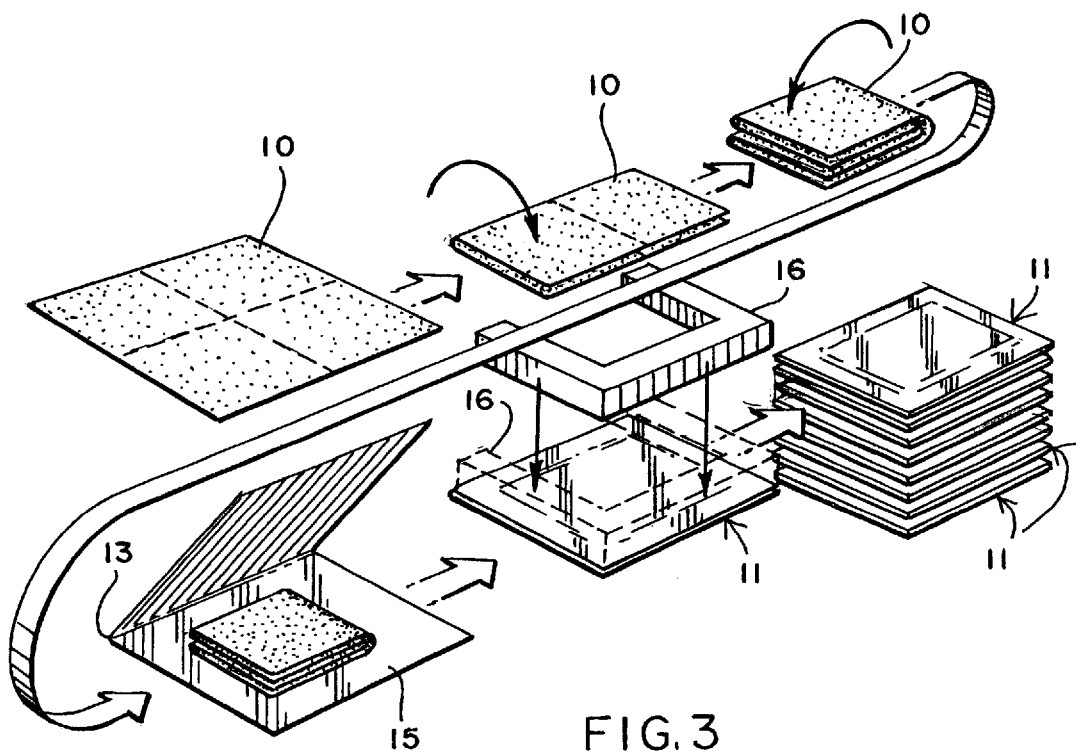
FIG. 3 is a diagrammatic flow sheet of the packaging of the acne pads by means of a Bartelt machine.
Figure 4:
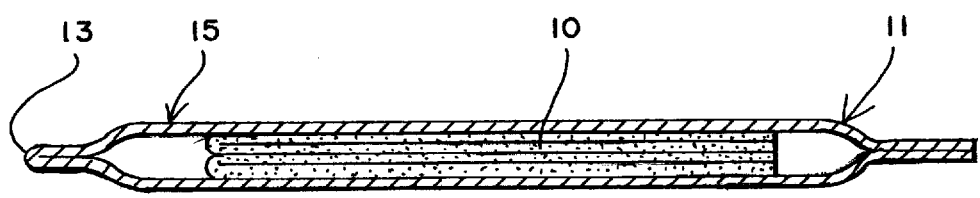
FIG. 4 is an enlarged cross-sectional view of an illustrative packet.

Turning now to the drawings, and FIGS. 1 and 2, it will be seen that the packaged acne pads 10 are formed on an endless string of adjacent packets 11 joined by a living hinge 13, and ideally in a quantity of twenty-two. After the acne pads 10 are folded, they go into a small box 12 which is closed and holds the packets 11 in place. Once the acne pad 10 has been impregnated, it is then ready to be encapsulated to form a packet 11. The acne pads are three inch squares folded twice to form a one and a half by one and a half inch pad for encapsulating in the packet. Ideally twenty-two packets are placed in a box 12. The reason for the twenty-two packets is that utilizing a three inch square folded twice to a packet of one and one-half inches gives a rectangular structure for the packaging which is highly efficient. Moreover, it minimizes the cost of the packaging process and the utilization of the packaging material as well as adapts itself to existing machinery and equipment for the packaging.

As to specifics of the packets 11 themselves, they are formed from an NP3850 paper/foil/polyester/polyethylene material. That material is employed in the package. The impregnated pads 10 are formed of 75 gram 149–189 tight waffle Novonette. The same are formed by passing endlessly and dropping down into a solution and subsequently rolled to remove excess fluid per three inch square acne pad, distributed uniformly across the pad.

| | |
|---|---|
| De-ionized water | 74.138 |
| SD Alcohol 40 | 24.000 |
| Witconate 1240 Slurry | 0.750 |
| Salicylic Acid | 0.550 |
| Fragrance | 0.200 |
| Citric Acid | 0.200 |
| Sodium Carbonate | 0.150 |

| | |
|---|---:|
| Menthol | 0.002 |
| Simethicone | 0.010 |
| Total | 100.000 |

The above ingredients can be varied, and some omitted, but the active ingredient which activates the cleansing action to address the problem of acne is salicylic acid. The above ingredients are known to be acceptable for the treatment of acne, particularly if SD Alcohol 40 is employed.

The reason for the twenty-two packets is that utilizing a three inch square folded twice to a packet of one and one-half inches gives a rectangular structure for boxing which is highly efficient, and minimizes the cost of the packed material as well as the machinery and equipment available for the packaging.

In order to maintain the highest level of control over the formation of the acne pads and thereafter the packaging, the following steps are undertaken. The formulation, after developing the aggregate, is tested to stringent levels of microbiological examination. A qualified abrasive active ingredient levels are verified by high pressure liquid carbon dioxide analysis. Packet samples are taken and tested for compliance to specifications, quarantined for drug stability verification, and tested rigorously for seal integrity, fill weights, aesthetics, etc. Quality control inspection is performed, both during and after manufacture of the packets. Further testing is performed on raw materials prior to packaging, including but not limited to, laminate analysis heat seal, water purity, correctness of copy, compliance of chemicals to standards and purity.

Finally, the machine employed ideally for packaging is a Bartelt-type horizontal pouch packager which is loaded, both as to packaging material and product as follows.

A printed roll of foil laminate 15 is loaded on the packaging machine (not shown) and threaded through pull rollers. The rollers pull the laminate over a plow which folds it in half (forming the front and back of the packet). The first machine states moves a U-shaped seal forming the sides and bottom of the pouch. An electric eye at the second station "reads" the packer's printed eye mark and registers the laminate (so each pouch is only one front and back). At the third station, slitter knives form the separation of the packets 11 and cut two impressions so they may be grabbed by the packet clamps at the fourth station. The clamps hold the packets in place for the insertion of the wiping material and liquid. At the fifth station, a towel folding and cutting station, the wiping material is folded once in the cross-direction, cut to the appropriate length, and inserted into the packet by "fingers" which makes the machine direction fold as it inserts the applicator into the packet. The liquid is added at station six through a precision pumping system. Stations seven, eight, and nine make the seal 16 on the pouch, quench the seal at a cooling bar station and emboss a code expiration date on the pouch. Station ten picks the packets off the clamp chain with suction cups 4 and places the tandem on a conveyor belt for pack off.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. An individually packaged disposable single acne pad formed from a square of non-bordered, non-woven synthetic waffle material substrate impregnated with an active anti-acne composition folded twice to form a package of four layers, each of which has a fold-line shared with an adjacent layer; wherein said single acne pad has an area of less than 10 square inches;

said acne pad being secured inside a non-resealable moisture sealing pocket; and said active anti-acne by percentage of weight the following ingredients of composition comprising as:

| | |
|---|---:|
| De-ionized water | 74.888 |
| SD Alcohol 40 | 24.000 |
| Salicylic acid | 0.550 |
| Fragrance | 0.200 |
| Citric Acid | 0.200 |
| Sodium Carbonate | 0.150 |
| Menthol | 0.002 |
| Simethicone | 0.010 |
| Total | 100.000. |

2. An individually packaged disposable single acne pad formed from a square of non-bordered, non-woven synthetic waffle material substrate impregnated with an active anti-acne composition folded twice to form a package of four layers, each of which has a fold-line shared with an adjacent layer; wherein said single acne pad has an area of less than 10 square inches;

said acne pad being secured inside a non-resealable moisture sealing pocket; and said active anti-acne composition comprising de-ionized water, SD Alcohol 40, salicylic acid, fragrance, citric acid, sodium carbonate, menthol, and simethicone.

* * * * *